(12) United States Patent
Vladimirsky et al.

(10) Patent No.: US 9,594,030 B2
(45) Date of Patent: Mar. 14, 2017

(54) LITHOGRAPHIC APPARATUS AND DEVICE MANUFACTURING METHOD

(75) Inventors: Yuli Vladimirsky, Weston, CT (US); Robert Tharaldsen, Sherman, CT (US)

(73) Assignee: ASML HOLDING N.V., Veldhoven (NL)

( * ) Notice: Subject to any disclaimer, the term of this patent is extended or adjusted under 35 U.S.C. 154(b) by 0 days.

(21) Appl. No.: 14/351,826

(22) PCT Filed: Sep. 14, 2012

(86) PCT No.: PCT/EP2012/068049
§ 371 (c)(1),
(2), (4) Date: Jun. 3, 2014

(87) PCT Pub. No.: WO2013/064298
PCT Pub. Date: May 10, 2013

(65) Prior Publication Data
US 2014/0264054 A1   Sep. 18, 2014

Related U.S. Application Data

(60) Provisional application No. 61/554,309, filed on Nov. 1, 2011.

(51) Int. Cl.
*G01J 1/42* (2006.01)
*G01N 21/956* (2006.01)
(Continued)

(52) U.S. Cl.
CPC ......... *G01N 21/956* (2013.01); *G01N 21/94* (2013.01); *G01N 21/9501* (2013.01); *G03F 1/84* (2013.01); *G03F 7/7065* (2013.01)

(58) Field of Classification Search
CPC ............... G03H 2222/45; G01N 21/4795
(Continued)

(56) References Cited

U.S. PATENT DOCUMENTS 5,923,423 A    7/1999   Sawatari et al.
6,597,446 B2 *  7/2003   Marks et al. ............. 356/237.2
(Continued)

FOREIGN PATENT DOCUMENTS

EP      0 598 582      5/1994
JP      H05-216211     8/1993
(Continued)

OTHER PUBLICATIONS

Hyper physics, published by Georgia State University, available at: http://hyperphysics.phy-astr.gsu.edu/hbase/optmod/holog2.html, available online as of Aug. 4, 2003.*
(Continued)

*Primary Examiner* — David J Makiya
*Assistant Examiner* — Kenneth J Malkowski
(74) *Attorney, Agent, or Firm* — Pillsbury Winthrop Shaw Pittman LLP (57) ABSTRACT

An apparatus and a method to detect a defect or particle on a surface that involves combining an object radiation beam redirected by the surface with a reference radiation beam having a plurality of intensities lower than the object radiation beam, to produce a plurality of patterns detected by a detector in order to detect the defect or particle on the surface from the patterns.

27 Claims, 6 Drawing Sheets

(51) Int. Cl.
 *G03F 7/20* (2006.01)
 *G03F 1/84* (2012.01)
 *G01N 21/94* (2006.01)
 *G01N 21/95* (2006.01)

(58) Field of Classification Search
 USPC .............. 250/559.1, 559.44–559.46,
 250/559.48–559.49; 356/237.4
 See application file for complete search history.

(56) References Cited

U.S. PATENT DOCUMENTS

| | | | |
|---|---|---|---|
| 6,608,321 B1* | 8/2003 | La Fontaine et al. ... | 250/559.44 |
| 7,061,625 B1 | 6/2006 | Hwang et al. | |
| 7,379,175 B1* | 5/2008 | Stokowski et al. ........ | 356/237.5 |
| 8,134,698 B1* | 3/2012 | Wolters et al. ............ | 356/237.1 |
| 2002/0159052 A1 | 10/2002 | Klooster et al. | |
| 2006/0091334 A1* | 5/2006 | Urbach et al. ........... | 250/559.45 |
| 2007/0030477 A1 | 2/2007 | Hwang et al. | |
| 2012/0081684 A1 | 4/2012 | Den Boef et al. | |

FOREIGN PATENT DOCUMENTS

| | | |
|---|---|---|
| JP | 2009-218651 | 9/2009 |
| WO | 2011/091877 | 8/2011 |

OTHER PUBLICATIONS

International Preliminary Report on Patentability mailed May 15, 2014 in corresponding International Patent Application No. PCT/EP2012/068049.

International Search Report mailed Dec. 18, 2012 in corresponding International Patent Application No. PCT/EP2012/068049.

Japanese Office Action mailed Jul. 28, 2016 in corresponding Japanese Patent Application No. 2014-537537.

Taiwan Office Action dated Jul. 13, 2016 in corresponding Taiwan Patent Application No. 101136262.

* cited by examiner

LITHOGRAPHIC APPARATUS AND DEVICE MANUFACTURING METHOD

This application is the U.S. national phase entry of PCT patent application no. PCT/EP2012/068049, filed Sep. 14, 2012, which claims the benefit of priority of U.S. provisional application No. 61/554,309, which was filed on Nov. 1, 2011.

FIELD

The present invention relates to a lithographic apparatus and a device manufacturing method.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

SUMMARY

It is not uncommon, for example, for a lithographic system and/or process to generate and/or be contaminated by one or more unwanted defects and/or particles. Such a defect and/or particle may be present on one or more various surfaces (e.g., a surface of a patterning device (e.g., a mask), a substrate and/or an optical element) and may cause erroneous exposure of the substrate. To detect and identify such a defect and/or particle, a multi-beam imaging technique may be used. Multi-beam imaging may be based on interferometric and/or holographic recording, followed by restoration of the image generated from the multi-beam imaging. To facilitate quality image restoration, high visibility of fringes generated in an interferometric and/or holographic detection is desired. High fringe visibility may be achieved by using a reference radiation beam having an intensity level substantially equal to or higher than an intensity level of the object beam used to image the surface that may potentially have such a defect and/or particle. Such an arrangement is conducive for restoration of only those features that are comparable to or larger than a minimum resolving power or resolution spot of an objective lens in an optical system of the multi-beam imaging apparatus. However, such an arrangement fails to image or detect a particle and/or defect of a size significantly smaller than the minimum resolution spot of the optical system. This is due to the fact that when the object radiation beam is incident on the surface having the defect or particle, the wave phase information associated with the defect or particle, is effectively masked by the wave phase information of an area adjacent that defect or particle.

It would be advantageous, for example, to provide an arrangement and/or method to detect defects and/or particles smaller than a minimum optical resolution of a detection optical system or a detecting apparatus and/or method to direct an object radiation beam and a reference radiation beam to image such defects and/or particles.

According to an aspect of the invention, there is provided a method to detect a defect or particle on a surface comprising combining an object radiation beam redirected by the surface with a reference radiation beam having a plurality of intensities lower than the object radiation beam, to produce a plurality of patterns detected by a detector in order to detect the defect or particle on the surface from the patterns.

According to an aspect of the invention, there is provided a detecting apparatus comprising:

an optical element to receive an object radiation beam redirected by a surface; and a detector configured to receive a combination of the object radiation beam from the optical element and a reference radiation beam having a plurality of intensities lower than the object radiation beam, to produce a plurality of patterns detected by the detecting medium in order to detect the defect or particle on the surface from the patterns.

According to an aspect of the invention, there is provided a non-transitory computer readable storage medium having a computer program code stored therein which, when executed by a computer, causes a plurality of detected patterns to be processed to detect a defect or particle on a surface, the plurality of patterns detected by a detector and produced from combination of an object radiation beam redirected by the surface with a reference radiation beam having a plurality of intensities lower than the object radiation beam.

According to an aspect of the invention, there is provided a method for detecting a given defect or particle on a surface, the method comprising:

combining an object radiation beam redirected by the surface with a reference radiation beam set for a plurality of times each at a different intensity;

producing a plurality of corresponding optical patterns from the combination of the object radiation beam and the reference radiation beams each at a different intensity;

detecting the plurality of corresponding optical patterns with a detector; and processing the plurality of corresponding optical patterns to enable detection of the defect or particle on the surface when at least one intensity of the plurality of different intensities of the reference radiation beam is set such that the at least one intensity substantially matches an intensity of the object radiation beam associated with the defect or particle, the intensity associated with the defect or particle being less than an intensity of the object radiation beam incident on the surface.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
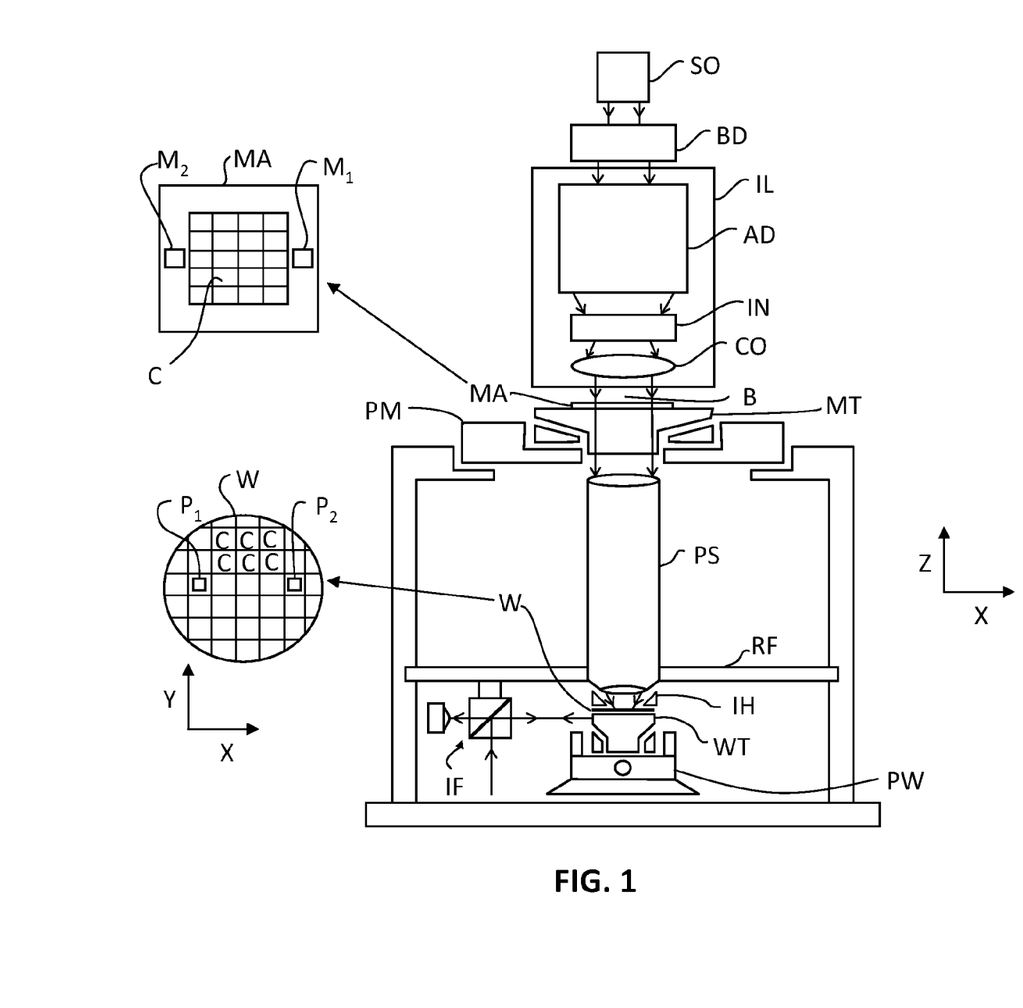
FIG. 1 schematically depicts a lithographic apparatus according to an embodiment of the invention.

FIG. 1 schematically depicts a lithographic apparatus according to an embodiment of the invention. The apparatus comprises:

an illumination system (illuminator) IL configured to condition a radiation beam B (e.g. ultraviolet (UV) radiation or deep ultraviolet (DUV) radiation);

a support structure (e.g. a mask table) MT constructed to support a patterning device (e.g. a mask) MA and connected to a first positioner PM configured to accurately position the patterning device MA in accordance with certain parameters;

a support table, e.g. a sensor table to support one or more sensors or a substrate table WT constructed to hold a substrate (e.g. a resist coated substrate) W, connected to a second positioner PW configured to accurately position the surface of the table, for example of a substrate W, in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system IL may include various types of optical components, such as refractive, reflective, magnetic, electromagnetic, electrostatic or other types of optical components, or any combination thereof, for directing, shaping, or controlling radiation.

The support structure MT holds the patterning device MA. It holds the patterning device MA in a manner that depends on the orientation of the patterning device MA, the design of the lithographic apparatus, and other conditions, such as for example whether or not the patterning device MA is held in a vacuum environment. The support structure MT can use mechanical, vacuum, electrostatic or other clamping techniques to hold the patterning device MA. The support structure MT may be a frame or a table, for example, which may be fixed or movable as required. The support structure MT may ensure that the patterning device MA is at a desired position, for example with respect to the projection system PS. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device MA may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix. Patterning device MA may have undesirable particles or surface defects on one or more surfaces thereof that can lead to an error in the pattern being exposed upon wafer W.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two or more tables (or stage or support), e.g., two or more substrate tables or a combination of one or more substrate tables and one or more cleaning, sensor or measurement tables. For example, in an embodiment, the lithographic apparatus is a multi-stage apparatus comprising two or more tables located at the exposure side of the projection system, each table comprising and/or holding one or more objects. In an embodiment, one or more of the tables may hold a radiation-sensitive substrate. In an embodiment, one or more of the tables may hold a sensor to measure radiation from the projection system. In an embodiment, the multi-stage apparatus comprises a first table configured to hold a radiation-sensitive substrate (i.e., a substrate table) and a second table not configured to hold a radiation-sensitive substrate (referred to hereinafter generally, and without limitation, as a measurement, sensor and/or cleaning table). The second table may comprise and/or may hold one or more objects, other than a radiation-sensitive substrate. Such one or more objects may include one or more selected from the following: a sensor to measure radiation from the projection system, one or more alignment marks, and/or a cleaning device (to clean, e.g., the liquid confinement structure).

In such "multiple stage" (or "multi-stage") machines the multiple tables may be used in parallel, or preparatory steps may be carried out on one or more tables while one or more other tables are being used for exposure. The lithographic apparatus may have two or more patterning device tables (or stages or support) which may be used in parallel in a similar manner to substrate, cleaning, sensor and/or measurement tables.

In an embodiment, the lithographic apparatus may comprise an encoder system to measure the position, velocity, etc. of a component of the apparatus. In an embodiment, the component comprises a substrate table. In an embodiment, the component comprises a measurement and/or sensor and/or cleaning table. The encoder system may be in addition to or an alternative to the interferometer system described herein for the tables. The encoder system comprises a sensor, transducer or readhead associated, e.g., paired, with a scale or grid. In an embodiment, the movable component (e.g., the substrate table and/or the measurement and/or sensor and/or cleaning table) has one or more scales or grids and a frame of the lithographic apparatus with respect to which the component moves has one or more of sensors, transducers or readheads. The one or more of sensors, transducers or readheads cooperate with the scale(s) or grid(s) to determine the position, velocity, etc. of the component. In an embodiment, a frame of the lithographic apparatus with respect to which a component moves has one or more scales or grids and the movable component (e.g., the substrate table and/or the measurement and/or sensor and/or cleaning table) has one or more of sensors, transducers or readheads that cooperate with the scale(s) or grid(s) to determine the position, velocity, etc. of the component.

Referring to FIG. 1, the illuminator IL receives a radiation beam from a radiation source SO. The source SO and the lithographic apparatus may be separate entities, for example when the source SO is an excimer laser. In such cases, the source SO is not considered to form part of the lithographic apparatus and the radiation beam is passed from the source SO to the illuminator IL with the aid of a beam delivery system BD comprising, for example, suitable directing mirrors and/or a beam expander. In other cases the source SO may be an integral part of the lithographic apparatus, for example when the source SO is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator IL can be adjusted. In addition, the illuminator IL may comprise various other components, such as an integrator IN and a condenser CO. The illuminator IL may be used to condition the radiation beam, to have a desired uniformity and intensity distribution in its cross section. Similar to the source SO, the illuminator IL may or may not be considered to form part of the lithographic apparatus. For example, the illuminator IL may be an integral part of the lithographic apparatus or may be a separate entity from the lithographic apparatus. In the latter case, the lithographic apparatus may be configured to allow the illuminator IL to be mounted thereon. Optionally, the illuminator IL is detachable and may be separately provided (for example, by the lithographic apparatus manufacturer or another supplier).

The radiation beam B is incident on the patterning device (e.g., mask) MA, which is held on the support structure (e.g., mask table) MT, and is patterned by the patterning device MA. It is to be noted that radiation beam B may be incident on the patterning device from a direction different from the one shown in FIG. 1. For example, radiation beam B may be incident from a position below the patterning device and may be reflected by the patterning device, or other surfaces (in contrast to being transmitted by the patterning device, as shown in FIG. 1). Having traversed the patterning device MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions C (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam B is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam B is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion C in a single dynamic exposure, whereas the length of the scanning motion determines the height (in the scanning direction) of the target portion C.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

As discussed above, undesirable particles and/or defects may occur on various surfaces and may occur by various reasons. For example, particles may be generated by mechanical rubbing of various parts in a lithographic apparatus and become located on an optical element, a substrate, a patterning device, a movable table, etc. Particles may be transported or generated by a fluid system or other movable component of a lithographic apparatus and similarly become located on an optical element, a substrate, a patterning device, a movable table, etc. For example, movement of a patterning device into and out of a lithographic apparatus before and after exposure, respectively, can bring particles into a lithographic apparatus or expose the patterning device to particles. Similarly, accidental collisions of the patterning device or the substrate can cause defects or particles on a surface of the patterning device/substrate. Presence of a defect and/or particle may cause an error in the final pattern that is exposed on the substrate. For example, a particle and/or defect may alter one or more characteristics of object beam including, for example, wave phase, frequency, and/or amplitude. Similarly, presence of a defect and/or particle in or on the exposed final pattern that may cause the device to be ineffective for its intended purpose.

While the description below refers to a surface of patterning device MA on which a particle and/or defect is detected, a particle and/or defect may be detected on any surface using the detection apparatus and/or method described herein. For example, the surface may belong to a wafer W in order to detect a defect and/or particle, before, during, or after exposure from radiation beam B. The given defect or particle may be a known defect or particle that can be analyzed using an embodiment of the invention, for example, to determine a size of the given defect or particle. Alternatively or additionally, the defect or particle may not be known, and is detected first and then analyzed.

Figure 2:
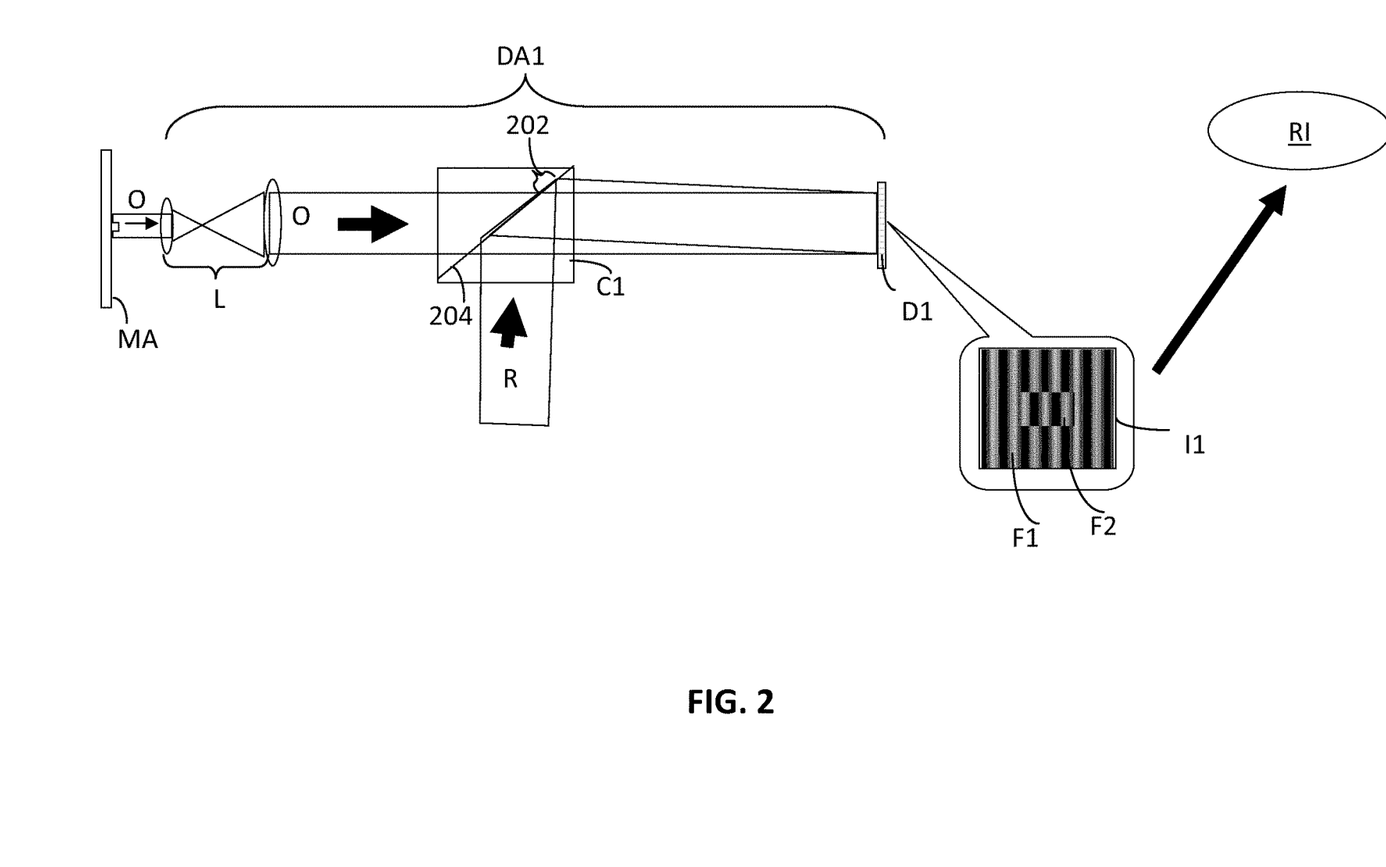
FIG. 2 depicts an arrangement to detect a defect or particle on a surface according to an embodiment of the invention.

FIG. 2 depicts an arrangement to detect a defect or particle on one or more surfaces. The arrangement of FIG. 2 shows a detecting or detection apparatus DA1 that includes, among other optical and electrical components, one or more lenses L optically coupled to a beam combiner C1, which is further optically coupled to a detector D1. An object radiation beam O is directed onto or through a surface of patterning device MA (using one or more optical elements not shown in FIG. 2 for convenience) and has an intensity level and/or phase altered (e.g., locally) due to the presence of a particle and/or a defect. The surface of patterning device MA can be smooth or patterned.

An optical element, e.g., formed by one or more lenses L receives object radiation beam O. One or more lenses L, through which object radiation beam O passes, may be any type of lenses. For example, one or more lenses L may be collimating lenses. After passage through one or more lenses L, object radiation beam O passes through beam combiner C1. In an embodiment, beam combiner C1 can be a dual beam combiner, such as those provided by JDS Uniphase Corporation of Milpitas, Calif., although other types of beam combiners (e.g., polarization beam combiners) could be used.

At beam combiner C1, a reference radiation beam R combines with object radiation beam O and an optical pattern I1 is provided at detector D1. At a surface 204 of combiner C1, reference radiation beam R is at a spatial offset 202 from object radiation beam O. Offset 202 may be programmable using a controller (not shown for convenience). This process of offsetting reference radiation beam R is known as spatial heterodyning, and in this arrangement reference radiation beam R acts as a spatial carrier for object radiation beam O. Since heterodyning of a spatial carrier with object radiation beam O is known, it will not be described herein.

In an embodiment, reference radiation beam R is at an intensity level that is lower than the intensity level of object radiation beam O. For example, the intensity level of reference radiation beam R is selected from a range of 0% to less than or equal to 30% of the intensity of object radiation beam O. When the intensity of reference radiation beam R is at 0% (i.e., reference radiation beam R is turned-off), the arrangement of FIG. 2 forms a coherent imaging system. By way of example only and not by way of limitation, a beam splitter or attenuator may be used to vary the intensity of reference radiation beam R.

In an embodiment, the combination of the object radiation beam O and the reference radiation beam R is detected at a plurality of different intensities of the reference radiation beam R lower than the intensity level of object radiation beam O. In an embodiment, a plurality of patterns similar to pattern I1 (which may comprise at least one interference pattern) resulting from the combination of object radiation beam O and reference radiation beam R at different intensities lower than the intensity level of object radiation beam O is detected. In an embodiment, the plurality of patterns may comprise at least one hologram resulting from the combination of object radiation beam O and reference radiation beam R. In an embodiment, pattern I1 includes a plurality of fringes F1 and F2 having respective dark and light fringe areas with respective fringe widths and fringe periods. When no defects or particles are present on the surface of patterning device MA, a regular pattern of fringes F1 without fringes F2 is obtained at detector D1.

Figure 5:
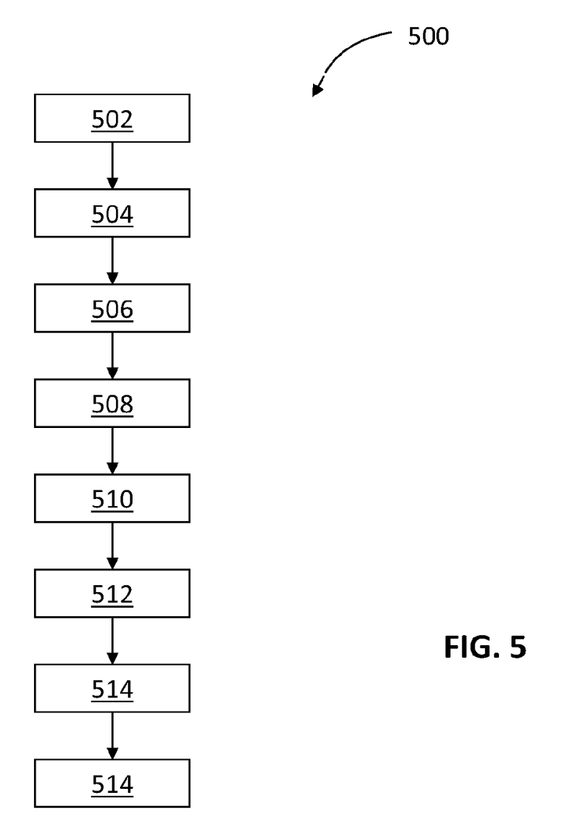
FIG. 5 depicts a method to detect a defect or particle on a surface according to an embodiment of the invention.

To detect the presence of a defect and/or particle on the surface, and to determine a size of the defect and/or particle, fringe patterns F1 and F2 captured at detector D1 are analyzed, as discussed in FIG. 5. In an embodiment, captured fringe patters F1 and F2 may be stored in a memory device (not shown). In an embodiment, detector D1 is a charge coupled device (CCD), a camera, or any other type of suitable recording medium to record pattern I1. Recorded pattern I1 is processed to obtain a restored image RI of the surface of patterning device MA according to one or more operations described in FIG. 5 below. For example, information in object radiation beam O and a complex conjugate of reference radiation beam R may be used to produce image RI using, e.g., a Fourier filtration technique.

Figure 3A:
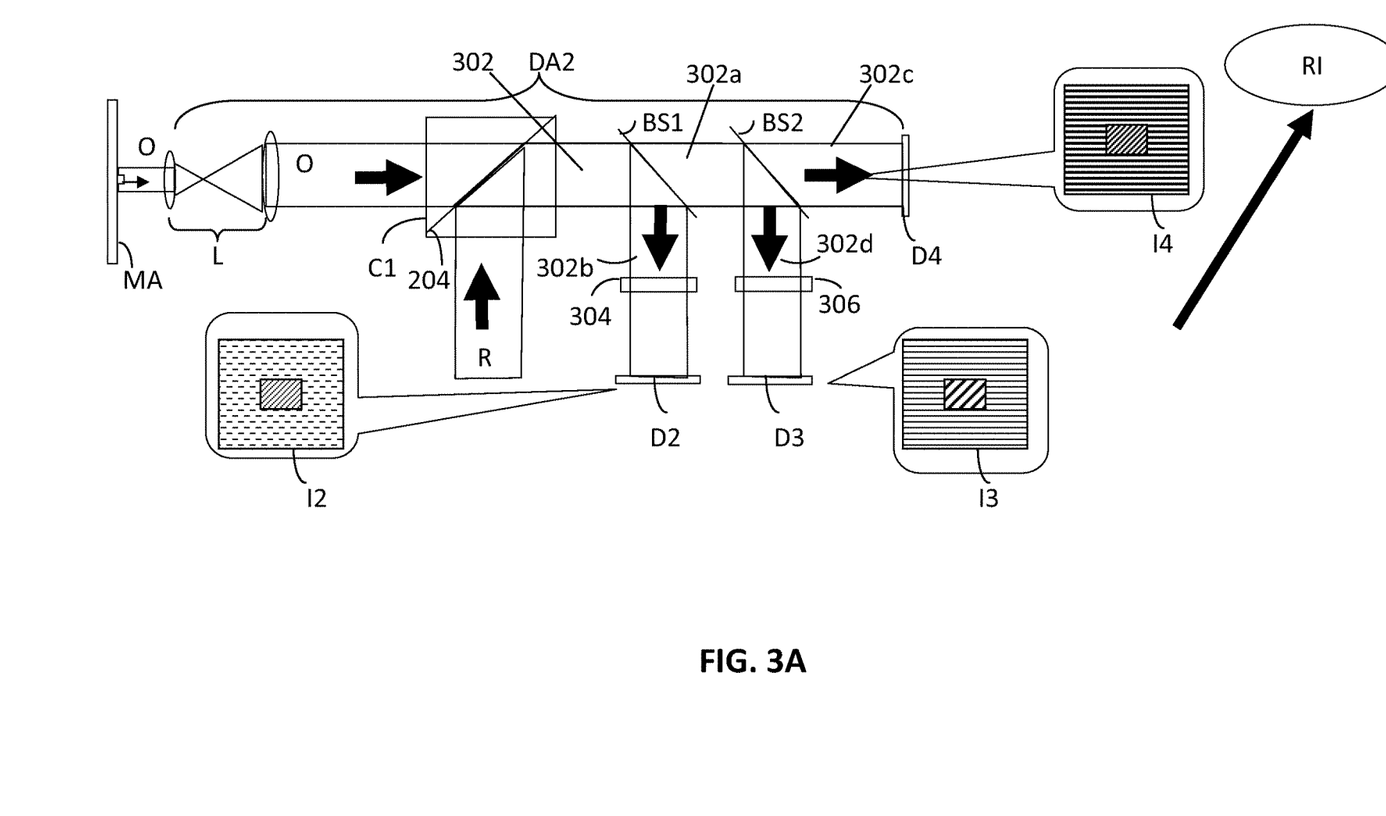
FIG. 3A depicts another arrangement to detect a defect or particle on a surface according to an embodiment of the invention.

Similar to FIG. 2, the arrangement in FIG. 3A is configured to detect a defect and/or particle on one or more surfaces. The arrangement of FIG. 3A shows a detection apparatus DA2 that includes, among other optical and electrical components, one or more lenses L optically coupled to a beam combiner C1, which is further optically coupled to beam splitters BS1 and BS2 and a detector D2. Detection apparatus DA2 additionally or optionally includes phase steppers or phase shifters 304 and 306 optically coupled to beam splitters BS1 and BS2, respectively. The surface on which a defect and/or particle is to be detected may be the same as the surface in FIG. 2, or may be a different surface.

The arrangement of FIG. 3A forms a parallel phase stepping detection and imaging system configured to detect a defect and/or particle, for example, using the method described in FIG. 5. Like FIG. 2, in FIG. 3A object radiation beam O is redirected by one or more surfaces of patterning device MA, collimated by one or more lenses L and combined at beam combiner C1 with reference radiation beam R. In FIG. 3A, reference radiation beam R is not spatially offset. The combination of reference radiation beam R and object radiation beam O, now referred to as a combination beam 302, provides at least one interference pattern or at least one hologram. Combination beam 302 is directed towards a beam splitter BS1. At beam splitter BS1, combination beam 302 is split into a beam portion 302a and a beam portion 302b, each at respective intensity levels.

Beam portion 302b is transmitted through phase stepper 304 and detected on a detector D2 as pattern I2. Beam portion 302a is further split using beam splitter BS2 into a beam portion 302c and 302d, each having respective intensities. Beam portion 302d is passed through phase shifter 306 and detected as a pattern I3 on detector D3. Beam portion 302c is detected as a pattern I4 on a detector D4. Amplitudes and phases of beam portions 302b, 302c, and 302d are functions of their respective intensities. In an embodiment, detectors D2, D3, and D4 are CCDs, cameras, or other types of suitable recording devices to detect, and optionally record, patterns I2, I3, and I4 for further processing.

Patterns I2-I4 are algebraically recalculated to form restored image RI of patterning device MA. For example, information in object radiation beam O and a complex conjugate of reference radiation beam R may be used to produce image RI algebraically.

Figure 3B:
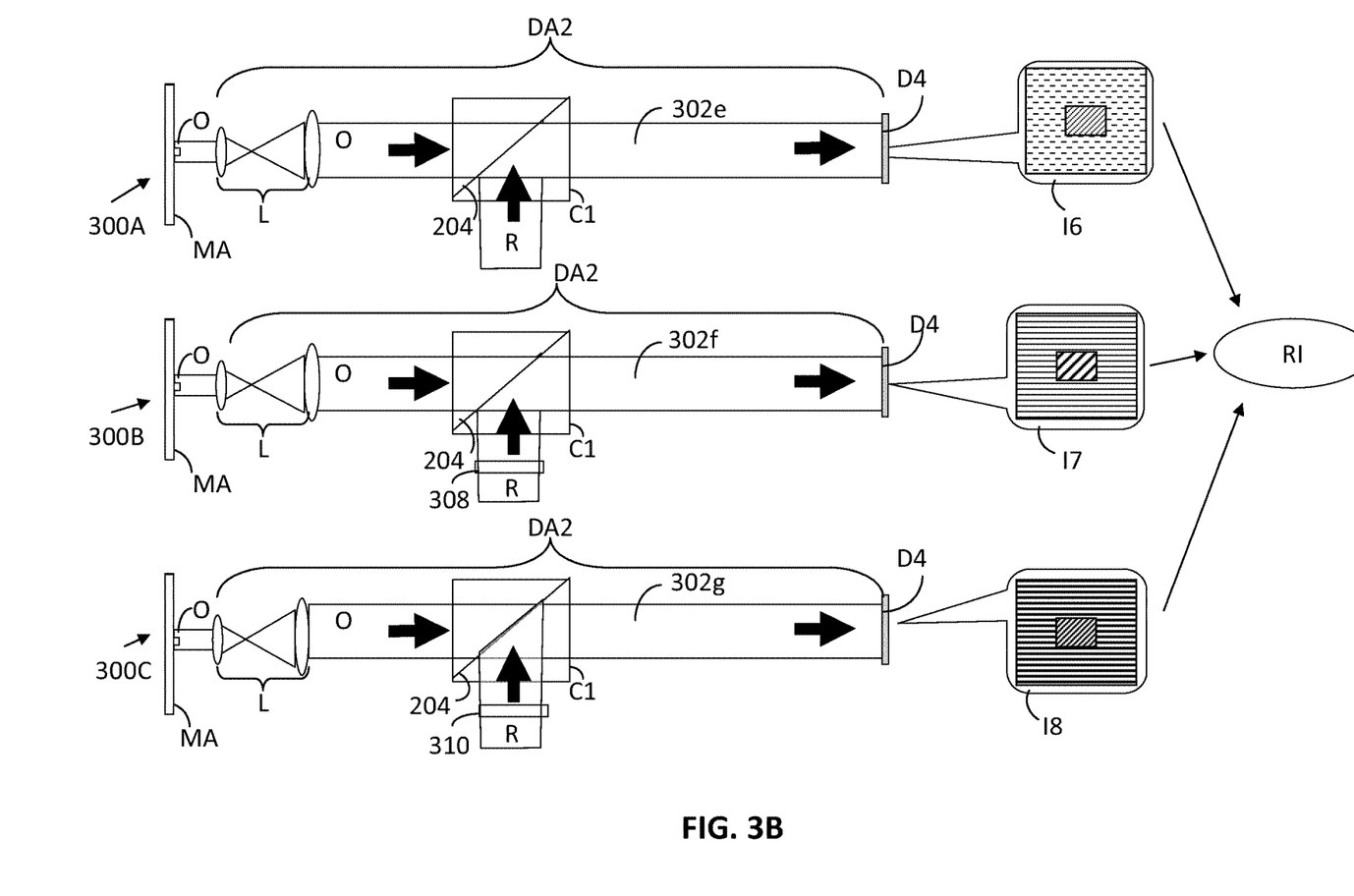
FIG. 3B depicts another arrangement to detect a defect or particle on a surface according to an embodiment of the invention.

In an embodiment, FIG. 3B illustrates an arrangement where detection apparatus DA2 includes different phase steppers to obtain different patterns I6-I8. Thus, instead of three detectors and two branches with phase steppers of FIG. 3A, the detection apparatus DA2 may have a single detector and one or more phase steppers are inserted into the optical path at different times to obtain the various patterns. For example, at an arrangement 300A at a particular point in time, detection apparatus DA2 does not include a phase stepper in the path of, e.g., the reference radiation beam R and produces a pattern I6 at detector D4 from a combination beam 302e. At an arrangement 300B at a particular point in time, the detection apparatus DA2 does include a phase stepper in the optical path. For example, prior to incidence upon beam combiner C1, reference radiation beam R is incident upon and is redirected by phase stepper or shifter 308 that alters a phase of reference radiation beam R by a first value. Such phase stepping of reference radiation beam R results in a pattern I7 at detector D4, different from pattern I6, from a combination beam 302f. Likewise, in an arrangement 300C at a further different time, one or more additional phase steppers or shifters (e.g., phase stepper 310) or one or more different phase steppers or shifters (e.g., phase stepper 310) that alter a phase of reference radiation beam R by a second value is used to create a pattern I8 at detector D4 from a combination beam 302g. Further, in an embodiment, one or more similar phase steppers or shifters (not shown) may be provided, additionally or alternatively, upon which object radiation beam O is incident and is redirected prior to incidence upon beam combiner C1. Furthermore, addition of phase steppers at various points in the beam path of reference radiation beam R and object radiation beam O to alter phases thereof may occur incrementally or decrementally. For example, the phase of the beams may be increased stepwise or decreased stepwise. Alternatively, such phase stepping may be carried out for random phase values stepped using a plurality of phase steppers. Embodiments of the invention are not restricted by positions of the one or more phase steppers or shifters (e.g., phase stepper or shifter 308 and/or 310), and other positions of phase steppers or shifters may be used to generate a range of patterns corresponding to different images of the surface(s) of patterning device MA.

Similar to FIG. 3A, patterns I6-I8 are algebraically recalculated to form restored image RI of patterning device MA, although an additional or alternative image processing technique for optical patterns, e.g., a Fourier transform technique, could be used. For example, information in object radiation beam O and a complex conjugate of reference radiation beam R at the different phase stepped values resulting from passage through phase steppers 308 and 310 may be used to produce image RI algebraically.

Figure 4:
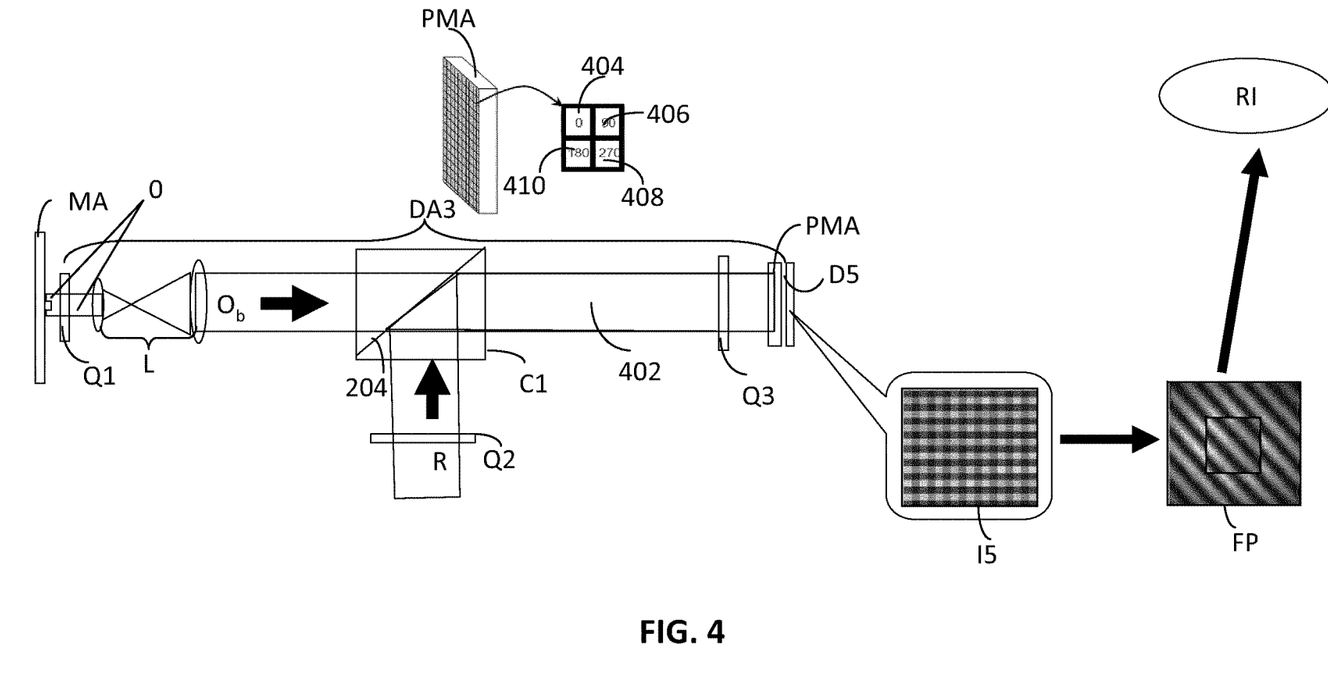
FIG. 4 depicts another arrangement to detect a defect or particle on a surface according to an embodiment of the invention.

Referring to FIG. 4, a further arrangement to detect a defect and/or particle on a surface is depicted. The arrangement of FIG. 4 shows a detection apparatus DA3 that includes, among other optical and electrical components, one or more lenses L optically coupled to a quarter wave plate Q1 through which object radiation beam O after redirection from one or more surfaces of patterning device MA is passed. One or more lenses L are optically coupled to beam combiner C1. The detection apparatus optionally includes a quarter wave plate Q2 that modifies reference radiation beam R prior to combination at surface 204 of beam combiner C1. Beam combiner C1 is optionally coupled to a quarter wave plate Q3 upon which a combination beam 402 is incident. Quarter wave plate Q3 is optically coupled to a pixelated phase mask PMA, which is further optically coupled to detector D5. Although quarter-wave plates Q1, Q2, and Q3 are shown in detection apparatus DA3, other elements (e.g., half wave plates) may be used. The arrangement shown in FIG. 4 is referred to as a pixelated phase mask interferometer.

Object radiation beam O and reference radiation beam R combine at surface 204 of beam combiner C1. In an embodiment, reference radiation beam R may be spatially offset from object radiation beam O. Beam combiner C1 produces combination beam 402 that passes through quarter wave plate Q3 before being incident upon pixelated phase mask PMA. Pixelated phase mask PMA includes pixel regions having different phase modifying properties. For example, in the embodiment shown in FIG. 4, pixelated phase mask PMA includes pixel regions 404, 406, 408, and 410 that modify the phase of incident radiation (e.g., a portion of combination beam 402). For example, pixel region 404 modifies the phase of radiation incident thereupon by 0 degrees (i.e., it does not alter the phase), pixel region 406 modifies the phase of the radiation incident thereupon by 90 degrees, pixel region 408 modifies the phase of the radiation incident thereupon by 270 degrees, and pixel region 410 modifies the phase of the radiation incident thereupon by 180 degrees, although other values of phase modification and other numbers of pixel regions could be used. A pixelated phase mask is known and will not be further described here.

The output of the pixelated phase mask PMA is provided to detector D5 upon which pattern I5 is detected resulting from passage of combination beam 402 from pixelated phase mask PMA. In the embodiment shown in FIG. 4, using every fourth pixel of pattern I5, a fringe pattern FP is formed that is then processed, for example, by Fourier filtration to form the restored complex image RI. Image RI can then be analyzed to detect a defect and/or particle on one or more surfaces of patterning device MA.

Referring to FIG. 5, a method 500 to detect a defect or particle on a surface according to an embodiment of the invention is depicted. Method 500 begins with a surface (e.g., a surface of patterning device MA) exposed with radiation to produce the object radiation beam O.

At 502, object radiation beam O is combined or mixed with reference radiation beam R at, e.g., surface 204 of beam combiner C1. Reference radiation beam R is at a plurality of intensity levels that are lower than an intensity level of object radiation beam O. For example, combining is carried out for a plurality of intensity levels of reference radiation beam R varying with the range from 0% to 30% of the intensity level of the object radiation beam O. In an embodiment, reference radiation beam R may be spatially offset from object radiation beam O at beam combiner C1. Prior to combination with reference radiation beam R, object radiation beam O may be passed through one or more lenses L for, for example, collimation. In an embodiment, object radiation beam O may be passed through a wave plate (e.g., quarter wave plate Q1) after redirection from a surface of patterning device MA and prior to incidence on one or more lenses L. Similarly, prior to combination with object radiation beam O, reference beam R may be passed through a wave plate (e.g., quarter wave plate Q2), as shown in FIG. 4. In an embodiment, the combined beam 402 may be passed through another wave plate (e.g., quarter wave plate Q3) and is thereafter, for example, incident upon a pixelated phase mask PMA, as shown in FIG. 4.

At 504, as a result of the combination of object radiation beam O with the reference radiation beam R at the various different intensity levels, a pattern(s) (e.g., I1-I5) is generated for each intensity level of reference radiation beam R resulting in a plurality of the patterns. For example, the plurality of patterns include at least one interference pattern or at least one holographic pattern. In an embodiment, at least one of the patterns is generated with reference radiation beam R turned off, which may result in a detectable interference pattern from the object radiation beam and radiation redirected by the particle and/or defect. In an embodiment, reference radiation beam R is at a very low intensity level compared to the intensity level of object radiation beam R (e.g., at 1% of the intensity level of object radiation beam O). By reducing the intensity level of reference radiation beam R close in value to the intensity of radiation redirected by the defect and/or particle on the surface (also referred to as "intensity matching"), enhanced sensitivity and/or detectability of a small particle and/or defect is achieved. Thus, even though the contrast of the fringes may be reduced significantly, the detection of a sub-resolution particle and/or defect is increased. In an embodiment, after combination at beam combiner C1, combination beam 302 may be passed through one or more beam splitters (e.g., beam splitters BS1 and BS2) to generate additional patterns from the pattern in combination beam 302 (e.g., patterns I2 and I3 shown in FIG. 3A).

At 506, the plurality of patterns are captured by a detector (e.g., detector D1) and are, for example, recorded on a recordable medium of a memory device medium. For example, a CCD may be used to record the plurality of patterns.

At 508, a set of images RI representative of the surface imaged by object radiation beam O is restored by processing the patterns, using for example, a computer processor. In an embodiment, the patterns include one or more holograms that are processed to restore an image of the surface of patterning device MA. Restoration of an image RI can be carried out using a phase and/or amplitude detection technique. Alternatively or additionally, image RI may be generated using a pseudo-restoration method including averaging hologram(s) intensities within an area(s) equivalent to a fringe period of the recorded patterns. The recorded patterns may be processed, for example, using a Fourier filtration technique or algebraic restoration technique that utilizes information in object radiation beam O and a complex conjugate of reference radiation beam R to reconstruct the set of images.

At 510, potential presence of a defect and/or particle on the surface of patterning device MA is facilitated by subtracting a local mean intensity (i.e., an average intensity in the area adjacent the intensity value under consideration) from all, or a plurality of, the intensity values of the image. For example, 10-15 adjacent pixels to a pixel under consideration are averaged and the average is subtracted from the pixel under consideration. Such subtraction may be carried out using, for example, moving average intensity value of a square, rectangle, circle, or ellipse shaped area of the image. Additionally or optionally, a method of weighted moving average, such as sliding or rolling paraboloid or other weight shape, could be used for averaging.

At 512, based upon subtracting the local mean intensity, a two-dimensional map of intensities is created, although additional parameters may be used to create higher dimensional maps (e.g., a three-dimensional map). In an embodiment, the two-dimensional map includes absolute intensity values, which facilitates "dark" and "bright" localities being detected to reveal potential defects and/or particles.

At 514, a threshold criterion is applied over the two dimensional map to accept or reject the presence of a particle and/or defect. In an embodiment, the threshold criterion is a certain signal-to-noise ratio for the two-dimensional map. In an embodiment, the signal-to-noise ratio is compared with intensity values of the two-dimensional map. If the intensity value is greater than the signal-to-noise ratio, a particle and/or defect is indicated as detected. In an embodiment, when at least one restored image meets the threshold criterion, a defect and/or particle is indicated as detected. In an embodiment, a plurality of restored images may be used to confirm the presence of the defect and/or particle. Such confirmation is arrived at, for example, when at least one of a set of restored images reveals that an intensity value in the map is greater than a predefined value for the signal-to-noise ratio.

At 516, once detected, a size of the particle and/or defect may be determined using a calibration technique. For example, a plurality of known-size particles (e.g., latex spheres) placed on a test specimen surface(s) may be detected using an apparatus described herein to yield associated intensity values and/or distributions, which can then be compared against the results of the method above to estimate the size of a detected particle and/or defect.

Using method 500, sub-resolution particles or defects can be detected as they are not obscured by high intensity levels of reference radiation beam R as used in conventional systems. Instead, by making intensity level of reference radiation beam R substantially lower (e.g., 70% lower) than the intensity level of object radiation beam O, wavefront distortion caused due to the presence of the particle or defect on the surface of patterning device MA is easily detected.

Method 500 of FIG. 5 is not limited to particular holographic or interferometric arrangements and/or settings such as those in FIGS. 2-4. Rather, method 500 can be applied to and utilized in a variety of interferometric or holographic arrangements, including, for example, one or more other types of phase stepping, single inclined reference beam, pixelated phase mask interferometers, and/or combinations thereof. Advantageously, method 500 enables less demanding setup stability, for example, for coherent imaging, although other advantages exist.

In an embodiment, method 500 may be carried out by a non-transitory computer readable storage medium having a computer program code stored therein which, when executed by a computer, causes a plurality of detected patterns to be processed to detect a defect or particle on a surface. The plurality of patterns are detected by a detector (e.g., detector D1) and produced from combination of object radiation beam O redirected by the surface with reference radiation beam R having a plurality of intensities lower than the object radiation beam.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The lithographic apparatus may also be of a type wherein a surface of the substrate is immersed in a liquid having a relatively high refractive index, e.g. water, so as to fill a space between a final element of the projection system and the substrate. Immersion liquids may also be applied to other spaces in the lithographic apparatus, for example, between the patterning device and a first element of the projection system. Immersion techniques are well known in the art for increasing the numerical aperture of projection systems.

The terms "radiation" and "beam" used herein encompass all types of electromagnetic radiation, including ultraviolet (UV) radiation (e.g. having a wavelength of or about 365, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions configured to cause performance of a method as disclosed above, or a computer-readable data storage medium (e.g. semiconductor memory, magnetic or optical disk) having such a computer program stored therein.

The descriptions above are intended to be illustrative, not limiting. Thus, it will be apparent to those skilled in the art that modifications may be made to the invention as described without departing from the scope of the claims set out below.

What is claimed is:

1. A method to detect a defect or particle on a surface comprising:
    combining an object radiation beam redirected by the surface, after the object radiation beam was redirected by the surface, with a reference radiation beam having a plurality of different intensities lower than the object beam and having a different intensity distribution than the redirected object radiation beam, to produce a plurality of patterns detected by a detector, the plurality of patterns comprising at least one interference pattern resulting from the combining of the object radiation beam and the reference radiation beam; and
    mathematically processing one or more of the detected patterns to restore an image of the surface from the one or more detected patterns, in order to detect the defect or particle on the surface from the image.

2. The method of claim 1, wherein the plurality of patterns comprises at least one hologram resulting from the combining of the object radiation beam and the reference radiation beam.

3. The method of claim 1, wherein the intensities of the reference radiation beam are selected from the range of 0% to less than or equal to 30% of the intensity of the object radiation beam.

4. The method of claim 3, wherein the intensity of the reference radiation beam is 0% of the intensity of the object radiation beam.

5. The method of claim 1, wherein the processing comprises restoring the image of the surface from the one or more detected patterns by using phase and/or amplitude information in the one or more detected patterns or by averaging intensities in the one or more detected patterns within an area equivalent to a fringe period of the one or more detected patterns.

6. The method of claim 1, wherein the processing comprises:
    subtracting a local mean intensity in an area of the one or more detected patterns and/or the image from an intensity value in the area;
    generating a two dimensional map of intensities based upon the subtracting; and
    applying a threshold criterion over the two dimensional map to accept or reject a presence of the defect or particle.

7. The method of claim 6, wherein the threshold criterion is a signal-to-noise ratio criterion.

8. The method of claim 6, wherein a size of the defect or particle is determined after the processing using calibration data.

9. The method of claim 1, wherein the surface is of a radiation beam patterning device.

10. The method of claim 1, wherein the detected defect or particle on the surface is of a size smaller than a minimum resolution of one or more optical components used to direct the object radiation beam and/or the reference radiation beam to the detector.

11. A detecting apparatus comprising:
    an optical system to receive an object radiation beam redirected by a surface and configured to combine the object radiation beam, after the object radiation beam was redirected by the surface, with a reference radiation beam having a plurality of different intensities lower than the object beam and having a different intensity distribution than the redirected object radiation beam;

a detector system configured to receive the combination of the object radiation beam from the optical element and the reference radiation beam having the plurality of intensities lower than the object radiation beam, to produce a plurality of patterns detected by the detector system, the plurality of patterns comprising at least one interference pattern resulting from the combining of the object radiation beam and the reference radiation beam; and a processor system configured to mathematically process one or more of the detected patterns to restore an image of the surface from the one or more detected patterns, in order to detect the defect or particle on the surface from the image.

12. The apparatus of claim 11, further comprising a beam splitter or attenuator to vary the intensity of the reference radiation beam.

13. The apparatus of claim 11, wherein the intensities of the reference beam are selected from the range of 0% to less than or equal to 30% of the intensity of the object radiation beam.

14. The apparatus of claim 13, wherein the intensity of the reference beam is 0% of the intensity of the object radiation beam.

15. The apparatus of claim 11, wherein the defect or particle is sized smaller than a minimum optical resolution of the detecting apparatus.

16. A non-transitory computer readable storage medium having a computer program code stored therein which, when executed by a computer, causes a plurality of detected patterns to be processed to detect a defect or particle on a surface, the processing comprising mathematically processing one or more of the detected patterns to restore an image of the surface from the one or more detected patterns, in order to detect the defect or particle on the surface from the image, wherein the plurality of patterns are detected by a detector and produced from combination of an object radiation beam redirected by the surface with a reference radiation beam having a plurality of different intensities lower than the object radiation beam and having a different intensity distribution than the redirected object radiation beam, wherein the combination is made after the object radiation beam was redirected by the surface and the plurality of patterns comprise at least one interference pattern resulting from the combining of the object radiation beam and the reference radiation beam.

17. The medium of claim 16, wherein the intensities of the reference radiation beam are selected from the range of 0% to less than or equal to 30% of the intensity of the object radiation beam.

18. A method for detecting a defect or particle on a surface, the method comprising:

combining an object radiation beam redirected by the surface, after the object radiation beam was redirected by the surface, with a reference radiation beam set for a plurality of times each at a different intensity;

producing a plurality of corresponding optical patterns from the combination of the object radiation beam and the reference radiation beams each at a different intensity, the optical patterns comprising interference fringe patterns from interference between the combined object radiation beam and reference radiation beams each at a different intensity;

detecting the plurality of corresponding optical patterns with a detector; and processing the plurality of corresponding optical patterns to enable detection of the defect or particle on the surface when at least one intensity of the plurality of different intensities of the reference radiation beam is set such that the at least one intensity substantially matches an intensity of the object radiation beam associated with the defect or particle, the intensity associated with the defect or particle being less than an intensity of the object radiation beam incident on the surface, the processing comprising recording a plurality of holograms corresponding to the plurality of interference fringe patterns, and restoring a set of images by processing the plurality of holograms.

19. The method of claim 18, further comprising:

generating a map of absolute intensity values by processing the set of restored images;

applying a signal-to-noise ratio criterion to the map of absolute intensity values; and confirming detection of the defect or particle when at least one restored image of the set of restored images reveals an intensity value greater than the signal-to-noise ratio.

20. The method of claim 18, wherein the intensity of the reference radiation beam is selected from a range of 0% to less than or equal to about 30% of the intensity of the object radiation beam incident on the surface.

21. The method of claim 1, wherein the plurality of patterns comprises a plurality of interference fringe patterns from interference between the combined object radiation beam and reference radiation beams each at a different intensity.

22. The method of claim 21, further comprising:

recording a plurality of holograms corresponding to the plurality of interference fringe patterns; and restoring a set of images by processing the plurality of holograms.

23. The apparatus of claim 11, wherein the plurality of patterns comprises a plurality of interference fringe patterns from interference between the combined object radiation beam and reference radiation beams each at a different intensity.

24. The apparatus of claim 23, wherein the detector system is further configured to record a plurality of holograms corresponding to the plurality of interference fringe patterns, and restore a set of images by processing the plurality of holograms.

25. The medium of claim 16, wherein the plurality of patterns comprises a plurality of interference fringe patterns from interference between the combined object radiation beam and reference radiation beams each at a different intensity and wherein the computer code further causes recording a plurality of holograms corresponding to the plurality of interference fringe patterns, and restoring a set of images by processing the plurality of holograms.

26. The medium of claim 16, wherein the processing comprises restoring the image of the surface from the one or more detected patterns by using phase and/or amplitude information in the one or more detected patterns or by averaging intensities in the one or more detected patterns within an area equivalent to a fringe period of the one or more detected patterns.

27. The apparatus of claim 11, wherein the processor system is configured to restore the image of the surface from the one or more detected patterns by using phase and/or amplitude information in the one or more detected patterns or by averaging intensities in the one or more detected patterns within an area equivalent to a fringe period of the one or more detected patterns.

* * * * *